(12) United States Patent
Weyer et al.

(10) Patent No.: US 8,425,932 B2
(45) Date of Patent: Apr. 23, 2013

(54) DELIVERY SYSTEM FOR REMOTE TREATMENT OF AN ANIMAL

(75) Inventors: Grant Weyer, Brisbane (AU); Simon Robert Sanford Trickey, Johannesburg (ZA); Timothy Donald Rose, Brisbane (AU)

(73) Assignee: SmartVet Pty Ltd., Taringa, Queensland (AU)

( * ) Notice: Subject to any disclaimer, the term of this patent is extended or adjusted under 35 U.S.C. 154(b) by 634 days.

(21) Appl. No.: 12/447,877

(22) PCT Filed: Oct. 31, 2007

(86) PCT No.: PCT/AU2007/001651
§ 371 (c)(1),
(2), (4) Date: Apr. 30, 2010

(87) PCT Pub. No.: WO2008/052263
PCT Pub. Date: May 8, 2008

(65) Prior Publication Data
US 2010/0203122 A1    Aug. 12, 2010

Related U.S. Application Data

(60) Provisional application No. 60/855,745, filed on Nov. 1, 2006.

(51) Int. Cl.
*A61K 9/64* (2006.01)
*A61K 9/66* (2006.01)

(52) U.S. Cl.
USPC .......................................... 424/456; 424/455

(58) Field of Classification Search ........................ None
See application file for complete search history.

(56) References Cited

U.S. PATENT DOCUMENTS

| 3,528,662 A | 9/1970 | Merchant et al. |
| 6,772,694 B1 | 8/2004 | Pearce et al. |
| 2002/0129728 A1 | 9/2002 | Vasel et al. |
| 2004/0089186 A1 | 5/2004 | Brygdes-Price |

FOREIGN PATENT DOCUMENTS

| JP | 07-143836 A | 6/1995 |
| WO | 96/03862 A1 | 2/1996 |
| WO | 02/060251 A2 | 8/2002 |
| WO | 2005074672 A2 | 8/2005 |
| WO | 2008/052263 A1 | 5/2008 |

OTHER PUBLICATIONS

Sun et al, Biomaterials Jan. 2005, 26 (1): 109-115.*
http://www.wired.com/dangerroom/2007/08/psycho-paintb-1/, Wired magazine, Aug. 2007.*
PCT—International Search Report for International Application No. PCT/AU2011/001173 dated Nov. 25, 2011.

* cited by examiner

*Primary Examiner* — Carlos Azpuru
(74) *Attorney, Agent, or Firm* — Morgan, Lewis & Bockius LLP

(57) ABSTRACT

A remote treatment delivery system comprising a substantially non-skin piercing dosage projectile containing a biologically active agent and a transdermal carrier.

28 Claims, No Drawings

DELIVERY SYSTEM FOR REMOTE TREATMENT OF AN ANIMAL

RELATED APPLICATIONS

The present application is a U.S. National Phase Application of International Application PCT/AU2007/001651, filed Oct. 31, 2007, which claims the benefit of U.S. Application No. 60/855,745, filed Nov. 1, 2006, all of which are herein incorporated by reference in their entirety.

TECHNICAL FIELD

The present invention relates to a remote delivery treatment system for commercial livestock and domestic animals and wildlife management.

BACKGROUND

In practice, it is frequently difficult and costly to deliver medicinal compounds to animals, especially if such animals are not kept in enclosures or specifically herded and contained for that purpose. Typically, during outbreaks of disease in wild animals, it is necessary to dart diseased animals in order to deliver the required medicinal compounds to the animals. This method of disease control and prevention is particularly stressful for the animals, and it is difficult to determine which animals have been darted, and which animals still need to be treated. In addition, using traditional systems, it is only possible to dart an animal with a single dose of a medicament—if more than one type of medicament is to be administered, the animal needs to be darted or injected more than once, or they need to be tranquilized individually, and then injected with the required medicaments.

The problem of treating animals, particularly wild animals, has been carried out in the past by development of delivery devices, such as darts and the like, that must pierce or penetrate the skin or tissue of the animal. Although these devices can effectively deliver the desired treatment, often the animal is exposed to the potential of post-treatment infections at the site of delivery. An additional problem with many of the prior art methods is that it can be, difficult to determine or monitor which animal has been treated.

Other methods for remotely delivering agents to animals or humans can involve providing of aerosols in close proximity to the animal or person to be treated from a projectile that does not penetrate the skin or tissue. An example of this form of delivery can be found in US 2002/0129728 in the name of Jaycor Tactical Systems. Although this system is particularly suitable for personnel or crowd control, it cannot deliver a defined dosage of a biologically active agent as a treatment regime to an animal. The dosage is variable and would depend on how much 'dust or powder' is taken up in the lungs.

WO 2005/074672 in the name of Simon Robert Trickey describes a frangible missile containing a treating substance that can be applied to the surface of an animal. Unfortunately, this system has very limited application as it can only provide treatment to the surface of the skin. Most veterinary medicines and chemicals, however, do not act directly on the surface of the skin so this system does not solve the problem of providing an effective remote delivery system for animals.

A number of prior art treatment systems require delivery of an agent by piercing the skin or tissue. Examples in this regard include U.S. Pat. No. 6,419,655 in the name of Gonex Inc, U.S. Pat. No. 6,584,910 in the name of David Plass, WO 00/71967 and US 2004/0089186 in the name of Richard Brydges-Price. Each of these systems can cause injury to an animal and are susceptible to causing post treatment infection at the site of impact.

The present inventors have developed a system that allows the remote delivery of a veterinary treatment to an animal without causing material injury to the animal.

SUMMARY OF INVENTION

In a first aspect, the present invention provides a remote treatment delivery system comprising:

a substantially non-skin piercing dosage projectile containing a biologically active agent and a transdermal carrier.

Preferably, the projectile comprises a frangible shell and the biologically active agent and transdermal carrier are housed within the shell of the projectile.

In a second aspect, the present invention provides a method of remotely treating an animal comprising:

launching a projectile of the delivery system according to the first aspect of the present invention at an animal;

impacting the projectile on the animal to cause release of the biologically active agent and the transdermal carrier onto the skin of the animal, wherein the transdermal carrier facilitates passage of the biologically active agent through the skin to provide treatment to the animal, wherein there is no substantial piercing of the skin by the projectile.

In a third aspect of the invention, the present invention provides use of a delivery system according to the first aspect of the present invention in a method of treating an animal.

Preferably, the animal is a wildlife or game animal such as deer or other antelope species or buffalo, commercial or production livestock such as cattle and horses or larger bodied feral animals such as horses, buffalo wild dogs, pigs, and the like.

Preferably, the animal is treated for a condition such as disease, parasite infestation or condition, dietary deficiency, or fertility.

More preferably, the condition is parasite infection or infestation.

Preferably, the biologically active agent is present at a concentration (% v/v) of from about 0.1% to 20%. More preferably, the biologically active agent is at a concentration (% v/v) of from 0.5% to 10%. More preferably, the biologically active agent is at a concentration (% v/v) of from 1% to 5%. It will be appreciated that the concentration of the biologically active agent will be related to the dosage required for a particular size of animal.

In one preferred form, the biologically active agent is a pharmacological agent. Preferably, the pharmacological agent is a veterinary pharmaceutical from the established class of macrocyclic lactones such as Ivermectin, eprinomectin, moxidectin, selamectin, doramectin, milbemycin, abamectin, cydectin and emamectin benzoate.

More preferably, the pharmacological agent is a parasiticide (endo and ecto). Preferably, the parasiticide is avermectin and derivatives thereof including ivermectin and abamectin.

The veterinary pharmaceutical can also be selected from synthetic pyrethroids such as flumethrin, deltamethrin, cypermethrin, cyfluthrin, fenvalerate, alphacypermethrin and pyrethrin.

The veterinary pharmaceutical can also be an insect growth regulator selected from the group consisting of yriproxifen, methoprene, cyromazine, lufenuron, diflubenzuron, fluazuron, dicyclanil and fluazuron.

The veterinary pharmaceutical can also be selected from amidines such as Amitraz. Amitraz is a triazapentadiene compound, a member of the amidine class of antiparasitic drugs used for treating external parasites. Alternate names for Amitraz may include, but are not limited to Aazdieno, Acarac, Amitraze, Avartin, Baam, Edrizan, Maitac, Mitac, Mitaban, Triatox, Triatix, Vapcozin Taktic, Triazid, Topline, Tudy, Ectodex, Garial, Danicut, Ovidrex, Acadrex, Bumetran, and Ovasyn.

The veterinary pharmaceutical can also be selected from other anthelmintics such as fipronil, imidacloprid, rotenone, Magnesium fluorosilicate, piperonyl butoxide, spinosyns, and benzimidazole anthelmintics and immunomodulators (e.g. Levamisole).

In another preferred form, the biologically active agent is a health supplement such as a vitamin or mineral.

Examples of suitable vitamins or minerals include, but not limited to, calcium, potassium, iron, thiamine and Vitamin B12.

The biologically active agent and transdermal carrier thereof may be made up a variety of suitable solvents or liquid combinations, such as, but not limited to, isopropyl alcohol; dipropylene glycol methyl-ether; butylated hydroxytoluene dipropylene glycol monomethyl-ether; methylene chloride; diethyl ether, ethanol, acetonitrile, ethyl acetate, benzyl alcohol and a combination of natural oils.

In another preferred form, the biologically active agent is a vaccine or immunogenic compound.

Examples of suitable vaccines include, but not limited to, PZP (Porcine Zona Pelucida), Foot and Mouth, Bovine Tuberculosis, Tuberculosis, and other compatible live or attenuated vaccines known to the art to expose a treated animal to pathogenic organisms in a manner that provokes an immune response.

In this preferred form, the composition may include one or more adjuvants to assist in the efficacy of the vaccine. Suitable adjuvants would be readily known to a person skilled in the art. It will be appreciated that the adjuvant may also act as a transdermal carrier to assist in the movement of the biologically active agent.

The biologically active agent may include drugs such as contraceptives, analgesics, anti-inflammatories, vasodilators, bronchodilators, diuretics, anti-histamines, tranquilizers, anti-fungals, vitamins, muscle relaxants, and anti-virals, anti-parasitic compositions, anthelmintics, acaricides, insecticides, and the like. Alternatively, or additionally, the biologically active agent may include a hormone such as a progesterone, estrogen, testosterone, derivatives thereof, and/or combinations of such hormones. The biologically active agent may also include protein-based agents, such as crude or purified cell lysates, sub-unit vaccines, protein-based antigen display systems, antigens, peptides, oligopeptides, or polypeptides that are absorbable through the skin of the animal when used in combination with a transdermal carrier, for example proteinaceous or glycoprotein-derived contraceptives, such as a zona pellucida based contraceptive, e.g. the Porcine Zona Pellucida (PZP) contraceptive.

The biologically active agent may include any suitable antigen to which an immune response is desired in an animal. Examples include, but not limited to, Foot and Mouth Disease, tuberculosis, *Vibrio cholera* cholera toxin, tetanus toxide, bacterial ADP ribosylating exotoxin (bARE), *Escherichia coli* heat-labile enterotoxin, and mutants and derivatives thereof, and may include a mixture of any such transcutaneous immunization compositions.

The biologically active agent and transdermal carrier thereof may be made up in any suitable solvent or liquid, such as, but not limited to, isopropyl alcohol; dipropylene glycol methyl-ether; butylated hydroxytoluene dipropylene glycol monomethyl-ether; methylene chloride; diethyl ether, ethanol, acetonitrile, ethyl acetate, benzyl alcohol and a combination of natural oils.

In use the transdermal carrier facilitates passage of the biologically active agent through the skin of an animal in need of treatment. In the case of a vaccine, the transdermal carrier may also act as an adjuvant or facilitate the passage of an adjuvant if used.

It is to be understood that any suitable transdermal carrier or solvent which facilitates transdermal absorption of the active ingredient may be used. Typically, the transdermal carrier includes carriers such as isopropyl alcohol, dipropylene glycol methyl-ether, butylated hydroxytoluene dipropylene glycol monomethyl-ether, 1-methoxy 2-propanol (glysolv PM/Icinol PM), Ethylene glycol monobutylether (butyl glyxolv/butyl icinol), Butyl di glysolv (butyl-icinol), Transcutol, propylene glycol (PG), N-methyl-2 pyrrolidone (NMP), methylene chloride, diethyl ether, ethanol, acetonitrile, ethyl acetate, benzyl alcohol and a combination of natural oils; ethylene glycol, propylene glycol, dimethyl polysiloxane (DMPX), oleic acid, caprylic acid, 1-octanol, ethanol (denatured or anhydrous), liposomal compositions, suitable plant oils, such as *Aloe vera* derivatives or sesame seed oil or derivatives thereof, acrylic polymers, rubber-based polymers, polysiloxane-based polymers, polyvinylpyrrolidone-based polymers, dimethylsulfoxide (DMSO), dimethylformamide (DMF), lecithin, Transfersomes® (IDEA AG). Transfersomes® are artificial vesicles designed to mimic a cell vesicle and deluver drugs or genetic material into a cell. The bounding membrane of a Transfersomes® is more flexible than that of a liposome, allowing it to deform and pass through openings in a barrier, such as the skin, whose diameters are much smaller than the average vesicle size. A Transfersomes® is a bi-component, most often vesicular, aggregate. The main functional characteristic of the aggregate is the extreme flexibility and permeability of its bilayer-like membrane coating. Its basis is the interdependency of local membrane shape and composition, which makes the bilayer self-regulating and self-optimising. The bilayer is thus capable of stress adaptation, via local and reversible bilayer component demixing. These characteristics make Transfersomes® into a device suitable for non-invasive and targeted drug delivery, inter alia across intact skin.

Additional transdermal carriers include, but are not limited to, ethosomes, azone, castor oil derivatives, such as ethoxylated castor oil, jojoba oil derivatives, corn oil derivatives, emu oil derivatives, or any other suitable transdermal or transcutaneous carrier or carrier composition.

Preferably, the transdermal carrier is propylene glycol, DMSO, alcohol or a more penetrant adjuvant known to the art.

The delivery system may further comprise a marker. The marker may be a non-toxic, physiologically acceptable dye, sufficient to mark the skin, coat or fur of an animal for a period of about 1 hour to about 72 hours, preferably about 24 to 48 hours. The marker may be a pharmaceutical, food, or cosmetic colorant, pigment, or dye. Examples of suitable marking components include liquid dyes, powder dyes, water soluble dyes, infra-red dyes, ultraviolet dyes, or dyes that glow in the dark (e.g., chemiluminescent dye's or phosphorescent dyes). It is to be understood that the dyes may be selected so as not to impair or interfere with the action or efficacy of the biologically active agent or the transdermal carrier.

The marker may be fluorescent, rendering animals which have been marked or treated under low-light conditions easily visible. The marker and/or solution may also contain a radioactive or other suitable tracking component.

Typically, the projectile is shot from a launching device such as a gun pressure or gas activated launcher or the like. Examples of potentially suitable launching devices may be based on similar gas discharge technologies utilized in current dart guns, air guns, crowd control guns and paintball markers currently in production and used in the veterinary, security, law enforcement, hunting, and recreational shooting or paintball industry.

The projectile is adapted to deliver the biologically active agent to the animal substantially without piercing the skin of the animal. Accordingly, the biologically active agent may be transported (with the aid of transdermal solvents) through the skin following rupturing of the projectile upon contact with the animal, penetration of the biologically active agent being effected by the transdermal carrier contained within the projectile.

The shell of the projectile may be made of any suitable encapsulating material, such as, for example, gelatine, linear polymers, or polystyrene derivatives, thin-walled plastics materials, hydrophilic colloidal materials such as, gelatin, albumin, gum arabic, alginate, casein, agar or pectins, or combinations thereof, or synthetic organic compounds such as, but not limited to, polystyrene, polypropylene, polyethylene, polycarbonate, polyamide, polysulfane, polyvinylchloride, resinous compounds such as fibreglass or Perspex derivatives, or combinations thereof.

Preferably, the frangible shell of the projectile is made of soft gelatine, glycerol and/or sorbitol and combinations thereof.

The biologically active agent and transdermal carrier may be encapsulated in one or more encapsulating or coating agents in order to more effectively control the delivery rate of the biologically active agent and transdermal carrier to the animal. The encapsulating or coating agent may be chosen such that it regulates the release of the biologically active agent once it has been absorbed into the blood stream or lymphatic system of the animal.

The projectiles may be launched with a single trigger action from a projectile launcher. The projectile launcher may include a selector for selecting the number of projectiles to be launched with a single trigger action. Alternatively, the projectiles may be delivered using a semi-automatic trigger action.

The projectiles, when used to deliver multiple biologically active agents or doses, may include biologically active agents which are similar or differing in composition, efficacy, or pharmaceutical action. Accordingly, it is to be understood that the dose administered to an animal may be controlled by selecting the number and type of dosage forms or projectiles to be launched at an animal. In this way, a user can easily adjust the dose required for correctly dosing the animal, by compensating for the size and weight of an animal, and tailor dosing regimens.

It will be appreciated that the treatment may be prophylactic.

The projectile launcher may include velocity selection means operable to select the velocity at which the projectile is launched. For example the velocity selection means may include pressure-regulating means operable to select the pressure at which the pressurized fluid is released.

The launching propellant may be a pressurized fluid, such as gas or air.

The present invention has the following advantages:
I. a bio mechanical system for the remote delivery of treatment to an animal from a safe or remote distance without need for immediate proximity to the animal
II. can include use of a gas propelled launcher and a soft dosage projectile projectile containing a liquid solution with substantially no solid matter likely to cause skin rupture or other impact site wound
III. enabling the topical administration of a biologically active agent of a suitably solubilised pharmacological agent or compound
IV. can include a marking compound
V. impact of projectile on an animal leads to transdermal absorption of a desired amount or dose of a biologically active agent so as to produce the required therapeutic, blood or health levels in the animal
VI. effective to treat by systemic action a disease or parasite infestation condition of the animal either at pasture or in its natural habitat and thereby avoiding:
   unnecessary stress and danger to the animal and/or its handlers
   the need for capture, herding or containment and associated risk of injury
   infliction of treatment site wounding and associated risk of secondary infection.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred embodiments will be described with reference to the following drawings and examples.

MODE(S) FOR CARRYING OUT THE INVENTION

Definitions

The term "animal" is to be accorded its widest meaning, and may include mammalian species, marsupials, and bird species.

The term "transdermal" as used herein is to be accorded its widest meaning, and may include transcutaneous administration.

The term "biologically active agent" (and its equivalents "medicament", "agent", "drug", "active agent" and "pharmaceutical") is intended to have the broadest meaning and includes at least one of any therapeutic, prophylactic, vaccine, antigenic, pharmacological, anti infective (antibiotic or antiseptic) or physiologically active substance, which is deliverable to an animal to produce a desired, usually beneficial, effect. More specifically, any suitable biologically active agent that is capable of producing a pharmacological response, localized or systemic, irrespective of whether therapeutic, diagnostic, or prophylactic in nature, is within the contemplation of the invention. It should be rioted that the biologically active agents can be used singularly or in combinations and mixtures as required.

Steroidal hormones can be used in the present invention and may include, in certain embodiments, but not limited to, estrogenically effective steroid hormones such as colpormon, conjugated estrogens, estradiol and estradiol esters.

Anti-infectives and mineral and vitamin supplements as specified, other biologically active agents or specific parasiticide and/or anthelmintic drugs which may be employed more specifically in embodiments of the invention include, but are not limited to:

Macrocyclic Lactones including the avermectins and milbemycins, for example Ivermectin, eprinomectin, moxidectin, selamectin, doramectin, milbemycin, abamectin, cydectin and emamectin benzoate.

Synthetic pyrethroids such as flumethrin, deltamethrin, cypermethrin, cyfluthrin, fenvalerate, alphacypermethrin and pyrethrin.

Insect Growth Regulators such as yriproxifen, methoprene, cyromazine, lufenuron, diflubenzuron, fluazuron, dicyclanil and fluazuron.

Other anthelmintics such as fipronil, imidacloprid, rotenone, Mg fluorosilicate, piperonyl butoxide, spinosyns and other suitable benzimidazole anthelmintics and immunomodulators (e.g. Levamisole).

In one embodiment, the biologically active agent is a transdermal immunization composition, including *Vibrio cholera* cholera toxin, tetanus toxoidtoxoid, bacterial ADP ribosylating exotoxin (bARE), Foot and Mouth Disease antigens, tuberculosis antigens, and/or *Escherichia coli* heat-labile enterotoxin, and/or mutants and derivatives thereof. It also includes a mixture of any such transdermal immunization compositions and/or other medicaments. The transdermal immunization compositions or mixtures thereof may be made up in any suitable solvent or liquid, such as, but not limited to, water or alcohol. The transdermal immunization compositions can further serve as transdermal carriers in their own right, in that they facilitate the dermal penetration of other biologically active agents, compositions, polypeptides, oligopeptides, or peptide fragments.

Steroidal hormones can be used in the present invention and may include, in certain embodiments, estrogenically effective steroid hormones such as colpormon, conjugated estrogens, estradiol and estradiol esters (e.g. acetate, benzoate, cypionate, dipropionate diacetate, enanthate, undecylate and valerate), estriol, estrone, ethinyl estradiol, equilenin, equilin, mestranol, moxestrol, mytatrienediol, quinestradiol and quinestrol; progestagenically effective steroid hormones such as allylestrenol, anagestone, chlormadinone acetate, delmadinone acetate, demegestone, desogestrel, 3-keto desogestrel, dimethisterone, dydrogesterone, ethinylestrenol, ethisterone, ethynodiol (and diacetate), fluorogestone acetate, gestodene, gestonorone caproate, haloprogesterone, (17-hydroxy- and 17-acetate-) 16-methylene-progesterone, 17α-hydroxyprogesterone (acetate and caproate), levonorgestrel, lynestrenol, medrogestone, medroxyprogesterone (and acetate), megestrol acetate, melengestrol, norethindrone (acetate and enanthate), norethisterone, norethynodrel, norgesterone, norgestimate, norgestrel, norgestrienone, 19-norprogesterone, norvinisterone, pentagestrone, progesterone, promegestone, quingestrone and trengestone; androgenically effective steroid hormones such as aldosterone, androsterone, boldenone, cloxotestosterone, dehydroepiandrosterone, fluoxymesterone, mestanolone, mesterolone, methandrostenolone, methyltestosterone, 17α-methyltestosterone, 17α-methyltestosterone 3-cyclopentyl enol ether, norethandrolone, normethandrone, oxandrolone, oxymesterone, oxymetholone, prasterone, stanolone, stanozolol, testosterone (acetate, enanthate, isobutyrate, propionate and undecanoate), testosterone-17-chloral hemi-acetal, testosterone-17β-cypionate, or tiomesterone.

Other biologically active agents or specific drugs which may be employed in embodiments of the invention include, but are not limited to:

Anaesthetic agents and analgesics, such as benzocaine, bupivicaine, capsaicin, cocaine, dibucaine, dyclonine, etidocaine, lidocaine, mepivacaine, prilocaine, procaine and tetracaine, acetaminophen, acetylsalicylic acid, buprenorphine, codeine, fentanyl, hydromorphone, lisuride, salicylic acid derivatives, sufentanil and sumatriptan.

Antibacterial or antibiotic agents such as aminoglycosides, δ-lactams, cephamycins, macrolides, penicillins, polypeptides and tetracyclines.

Anthelmintic, anti-trematodal, anticestodal, or anti-parasitic/parasiticidal agents such as albendazole, levamisole, mebendazole, pyrantel, praziquantel, moxidectin, ivermectin, oxamniquine, metrifonate, piperazine, thiabendazole, tiabendazole, diethylcarbamazine, pyrantel, niclosamide, doramectin, eprinomectin, morantel, oxfendazole, dichlorvos, chlorsulon and selamectin.

Acaricidal agents including antibiotic acaricides, nikkomycins, thuringiensin, macrocyclic lactones, acaricides, tetranactin, avermectin, acaricides, abamectin, doramectin, eprinomectin, ivermectin, selamectin, milbemycin, acaricides, milbemectin, milbemycin oxime, moxidectin, bridged diphenyl acaricides, azobenzene, benzoximate, benzyl benzoate, bromopropylate, chlorbenside, chlorfenethol, chlorfenson, chlorfensulphide, chlorobenzilate, chloropropylate, cyflumetofen, dicofol, diphenyl sulfone, dofenapyn, fenson, fentrifanil, fluorbenside, proclonol, tetradifon, tetrasul, carbamate acaricides, benomyl, carbanolate, carbaryl, carbofuran, methiocarb, metolcarb, promacyl, propoxur, oxime carbamate caricides, aldicarb, butocarboxim, oxamyl, thiocarboxime, thiofanox, dinitrophenol acaricides, binapacryl, dinex, dinobuton, dinocap, dinocap-6, dinocton, dinopenton, dinosulfon, dinoterbon, DNOC, formamidine acaricides, amidines, amitraz, chlordimeform, chloromebuform, formetanate, formparanate, mite growth regulators, clofentezine, diflovidazin, dofenapyn, fluazuron, flubenzimine, flucycloxuron, flufenoxuron, hexythiazox, organochlorine acaricides, bromocyclen, camphechlor, dienochlor, endosulfan, lindane, organophosphorus acaricides, organophosphate acaricides, chlorfenvinphos, crotoxyphos, dichlorvos, heptenophos, mevinphos, monocrotophos, TEPP, tetrachlorvinphos, organothiophosphate acaricides, amidithion, amiton, azinphos-ethyl, azinphos-methyl, azothoate, benoxafos, bromophos, bromophos-ethyl, carbophenothion, chlorpyrifos, chlorthiophos, coumaphos, cyanthoate, demeton, demeton-O, demeton-S, demeton-methyl, demeton-O-methyl, demeton-5-methyl, demeton-5-methylsulphon, dialifos, diazinon, dimethoate, dioxathion, disulfoton, endothion, ethion, ethoate-methyl, formothion, malathion, mecarbam, methacrifos, omethoate, oxydeprofos, oxydisulfoton, parathion, phenkapton, phorate, phosalone, phosmet, phoxim, pirimiphos-methyl, prothidathion, prothoate, pyrimitate, quinalphos, quintiofos, sophamide, sulfotep, thiometon, triazophos, trifenofos, vamidothion, phosphonate acaricides, trichlorfon, phosphoramidothioate acaricides, isocarbophos, methamidophos, propetamphos, phosphorodiamide caricides, dimefox, mipafox, schradan, organotin acaricides, azocyclotin, cyhexatin, fenbutatin, phenylsulfamide acaricides, dichlofluanid, phthalimide acaricides, dialifos, phosmet, pyrazole acaricides, acetoprole, fipronil, tebufenpyrad, vaniliprole, pyrethroid acaricides, pyrethroid ester caricides, acrinathrin, bifenthrin, cyhalothrin, cypermethrin, alpha-ypermethrin, fenpropathrin, fenvalerate, flucythrinate, flumethrin, fluvalinate, tau-fluvalinate, permethrin, pyrethroid ether acaricides, halfenprox, pyrimidinamine acaricides, pyrimidifen, pyrrole acaricides, chlorfenapyr, quinoxaline acaricides, chinomethionat, thioquinox, sulfite ester caricides, propargite, tetrazine acaricides, clofentezine, diflovidazin, tetronic acid acaricides, spirodiclofen, thiocarbamate acaricides, fenothiocarb, thiourea acaricides, chloromethiuron, diafenthiuron, unclassified acaricides, acequinocyl, amidoflumet, arsenous oxide, bifenazate, closantel, crotamiton, disulfiram, etoxazole, fenazaflor, fenazaquin, fenpyroximate, fluacrypyrim, fluenetil, mesulfen, MNAF, nifluridide, pyridaben, sulfiram, sulfluramid, sulfur triarathene.

Anti-fungal agents such as clortrimazole, ketoconazole, miconazole, nystatin and triacetin.

Antihistamine agents such as tricyclics such as ahistan, etymemazine, fenethazine, n-hydroxyethylpromethazine chloride, isopromethazine, mequitazine, promethazine, pyrathiazine, and thiazinamium methyl Anti-inflammatory and/or corticoid agents such as beclomethasone, betamethasone (and acetate, diproprionate and valerate), corticosterone, cortisone, deoxycortocosterone (and acetate), dexamethasone, diclofenac, fenoprofen, flucinolone (and acetonide), fludrocortisone, fluocinonide, flunisolide, fluradrenolide, flurbiprofen, halcinonide, hydrocortisone (and acetate), ibuprofen, ibuproxam, indoprofen, ketoprofen, ketorolac, naproxen, oxametacine, oxyphenbutazone, piroxicam, prednisolone, prednisone, suprofen and triamcinolone (and acetonide).

Antiviral agents such as acyclovir, rimantadine and vidarabine.

Anxiolytic agents such as azapirones such as buspirone and ipsapirone, benzodiazepines such as alprazolam, chlordiazepoxide, clonazepam, clorazepate, diazepam, flurazepam, halazepam, lorazepam, oxazepam, oxazolam, prazepam and triazolam.

β-Adrenergic agonist agents such as albuterol, carbuterol, fenoterol, metaproterenol, mirtazapine, rimiterol, quinterenol, salmefamol, soterenol, tratoquinol, terbutaline and terbuterol.

Bronchodilators such as ephedrine derivatives including

Anti-allergy agents such as amlexanox, astemizole, azelastine, cromolyn, fenpiprane, ibudilast, nedocromil, oxatomide, pentigetide, repirinast, tranilast and traxanox.

Cardioactive agents such as atenolol, benzydroflumethiazide, bendroflumethiazide, calcitonin, captopril, chlorothiazide, clonidine, clopamide, dobutamine, dopamine, diltiazem, enalapril, enalaprilat, gallopamil, indomethacin, isosorbide (dinitrate and mononitrate), monoxidil, nicardipine, nifedipine, nitroglycerin, papaverine, prazosin, procainamide, propranolol, prostaglandin $E_1$ and $E_2$, quinidine Central Nervous System stimulants and agents such as dextroamphetamine, methylphenidate, and nicotine.

Cholinergic agents such as acetylcholine, arecoline, bethanechol, carbachol, choline, methacoline, muscarine and pilocarpine.

Anti-cholinergic agents such as atropine, eucatropine and procyclidine. Anti-emetic agents such as acetylleucine monoethanolamine, alizapride, benzquinamide, bietanautine, bromopride, buclizine, chlorpromazine, clebopride, cyclizine, dimenhydrinate, dipheniodol, domperidone, granisetron, meclizine, methalltal, metoclopramide, metopimazine, nabilone, ondansteron, oxypendyl, pipamazine, piprinhydrinate, prochlorperazine, scopolamine, tetrahydrocannabinols, thiethylperazine, thioproperazine, trimethobenzamide and tropisetron.

Muscle relaxants such as Baclofen.

The term, "therapeutically effective" as used herein means an amount of a biologically active agent that is sufficient to achieve a desired local or systemic effect or result, such as to prevent, cure, mitigate or treat a disease or condition as required.

The amounts of the biologically active agent to be used in a projectile may be determined by methods known to persons skilled in the field of the invention. Amounts typically range from about 0.05 mg to about 20,000 mg, and preferably from about 0.1 mg to about 1,000 mg, depending on the biologically active agent, the disease to be treated, the animal species, the size of the animal and the transdermal carrier used. In certain embodiments of the invention, the biologically active agents may be included in a range from about 0.1 to about 500 mg per mammal per 50 kg body weight.

The term "transdermal carrier" or "transdermal carrier composition" as used herein refers to any material known in the art as being suitable for transdermal agent delivery administration, and includes any polymeric material into which an active agent may be solubilised in combination or admixture with the other ingredients of the composition. The term may also include enhancers, solvents, co-solvents, carriers and other types of additives useful for facilitating transdermal drug delivery, or adhesives for ensuring adhesion of the contents of the projectile to the skin, coat or fur of a target animal.

The transdermal carrier is typically used in an amount of about 1% to about 95%, and preferably from about 10% to about 75%, by weight based on the weight of the total carrier composition.

The transdermal carrier composition of the present invention can also contain one or more solvents and/or co-solvents known in the art.

Suitable solvents and co-solvents include volatile substances or compositions such as alcohols, aromatic hydrocarbons such as benzene derivatives, lower molecular weight alkanes and cycloalkanes, alkanoic acid esters, polyhydric alcohols, which include glycols, triols and, polyols such as ethylene glycol, diethylene glycol, propylene glycol, dipropylene glycol, trimethylene glycol, butylene glycol, polyethylene glycol, hexylene glycol, polyoxethylene, glycerin, trimethylpropane, sorbitol, polyvinylpyrrolidone, glycol ethers such as ethylene glycol monoethyl ether, glycol esters, glycol ether esters such as ethylene glycol monoethyl ether acetate and ethylene glycol diacetate; saturated and unsaturated fatty acids, mineral oil, silicone fluid, lecithin, retinol derivatives and the like, and ethers, esters and alcohols of fatty acids. or combinations and mixtures thereof.

Although the exact amount of solvents and co-solvents that may be used in the carrier composition depends on the nature and amount of the other ingredients, such amount typically ranges from about 0.1% to about 50%, and preferably from about 0.1% to about 30% by weight, and more preferably from about 1% to about 20%, by weight based on the dry weight of the total carrier composition.

The transdermal carrier is typically selected so that it may be readily absorbable by the skin of an animal without causing undue itching, irritation, or toxic effects to the animal. Selection of the transdermal carrier will also depend on the biologically active agent to be delivered to an animal and also the type of animal to be treated, or the intended delivery site on an animal. Thus, the transdermal carrier composition 16 may be selected to suit the charge, size, hydrophobicity, hydrophilicity, amphipathicity, pI, pH, decay rate, or other relevant criteria of the biologically active agent to be carried transdermally, while also being readily absorbable through the skin of an animal.

Typically, the transdermal carrier includes compounds such as isopropyl alcohol, dipropylene glycol methyl-ether, butylated hydroxytoluene dipropylene glycol monomethylether, methylene chloride, 1-methoxy 2-propanol (glysolv PM/Icinol PM), Ethylene glycol monobutylether (butyl glyxolv/butyl icinol), Butyl di glysolv (butyl-icinol), Transcutol, propylene glycol (PG), N-methyl-2 pyrrolidone (NMP), diethyl ether, ethanol, acetonitrile, ethyl acetate, benzyl alcohol and a combination of natural oils. ethylene glycol, propylene glycol, dimethyl polysiloxane (DMPX), oleic acid, caprylic acid, 1-octanol, ethanol (denatured or anhydrous), liposomal compositions, suitable plant oils, such as *Aloe vera* derivatives or sesame seed oil or derivatives thereof, acrylic polymers, rubber-based polymers, polysiloxane-based polymers, polyvinylpyrrolidone-based polymers, dimethylsulfoxide (DMSO), dimethylformamide (DMF), lecithin, Transfersomes®, ethosomes, azone, castor oil derivatives, such as ethoxylated castor oil, jojoba oil derivatives, corn oil derivatives, emu oil derivatives, or other suitable carriers.

In certain embodiments of the invention, an enhancer is incorporated into the carrier composition. The term "enhancers" as used herein refers to substances used to increase permeability and/or accelerate the delivery of an active agent through the skin of an animal, and include monohydric alcohols such as ethyl, isopropyl, butyl and benzyl alcohols; or dihydric alcohols such as ethylene glycol, diethylene glycol, or propylene glycol dipropylene glycol and trimethylene glycol; or polyhydric alcohols such as glycerin, sorbitol and polyethylene glycol, which enhance drug solubility; polyethylene glycol ethers of aliphatic alcohols (such as cetyl, lauryl, oleyl and stearly) including polyoxyethylene-4-lauryl ether, polyoxyethylene-2-oleyl ether and polyoxyethylene-10-oleyl ether; vegetable, animal and fish fats and oils such as cotton seed, corn, safflower, olive and castor oils, squalene, and lanolin; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide; salicylic acid; benzyl nicotinate; or higher molecular weight aliphatic surfactants such as lauryl sulfate salts, esters of sorbitol and sorbitol anhydride such as polysorbate. Other suitable enhancers include oleic and linoleic acids, triacetin, ascorbic acid, panthenol, butylated hydroxytoluene, tocopherol, tocopherol acetate, tocopheryl linoleate.

If enhancers are incorporated into the carrier composition, the amount typically ranges up to about 35%, and preferably from about 0.05% to about 20%, by weight based on the dry weight of the total carrier composition.

Use

Most current treatment methods require immediate proximity to the animal. In contrast, the present invention can provide remote delivery from a safe distance and is the only administration option which avoids capture, sedation or mustering/herding of animals. The incidence of secondary infection from needle site or treatment wound is particularly significant in the case of wild animal species (exposed to the elements) and is a material problem in the industry. Equally, the incidence of injury to animals and handlers when stock such as cattle are mustered, yarded and driven through a crush for individual dipping/treatment application can be a problem.

Prior art remote, projectile based delivery methods which do not deliberately pierce the skin (dart, syringe, silicon implant) are ineffective. The present inventors have developed a system for remote delivery/administration that can treat an animal systemically. The parasite treatments formulated only for dip or spray application must be administered to substantially the whole of the animals skin to effectively treat external parasites.

The reliable delivery of a full dosage is fundamentally important, particularly with parasiticides. Under dosing leads to mutation and rapid resistance build up. In terms of efficacy considerations, any treatment method which ensures delivery of an effective dose will therefore be favoured over those with arbitrary dosage characteristics. The present invention is adaptable for reliable dosage control matched only by injection.

Administration of biologically active agents by food/water additive, sprays etc is notoriously arbitrary. Individual dosage accuracy also has cost and environmental implications. Splash and spillage from dip treatment involves additional ingredient lost to wastage. It is generally unlawful to use or apply a pharmaceutical agent without regulatory license or authority. The product and any apparatus used to deliver it must meet the required standards of safety, efficacy and tolerance.

Most (if not all) of the current art methods can involve impact site injury or skin rupture of a scale unlikely to be acceptable to veterinary practitioners and/or the licensing authorities on both animal welfare and potential for secondary infection grounds.

The projectile according to the present invention does not cause rupture of the skin but the impact may cause mild bruising. Any bruising causes the local, blood vessels to dilate and rise to the under surface of the skin at the affected area. This increased blood flow at the delivery site potentially enhances the speed and extent of take up of the biologically active agent. This can lead to an increased efficacy result over a similar dosage of the same treatment compound applied topically by proximate pour on or spot on methods. Animal trial results have indicated that no unacceptable tissue damage is caused by the projectile hitting the skin and the impact site is fully normalised within days after treatment.

The present invention relates to the treatment of animals, especially wild animals or animals which may be free-ranging and not in captivity. Such animals are difficult or cumbersome to capture and treat using conventional methods. Most current methods for treating wild animals are highly stressful to the animals, and include darting the animals, chasing them into catch-nets or enclosures, or sedating them prior to administering treatment. The prior art methods are also dangerous to the persons administering such treatments, as darts have to be used containing potentially hazardous drugs including highly toxic morphine related drugs such as etorphine hydrochloride, and the risk of needle-stick or injury is high when attempting to dart as many animals as possible. Furthermore, in current methods it is often difficult for the person administering the treatment to determine which animals have been treated and which animals are still to be treated. This is especially difficult when treating the animals from an elevated area or from a helicopter.

The present invention is not limited to wildlife only, but also finds application in the treatment of commercial livestock, domestic animals and companion animals. In the case of cattle, use of the invention as described herein considerably lowers the stress levels of the animals, as compared to conventional dipping or inoculation techniques and reduces treatment process costs.

Typically, projectiles are made from a substance such as, but not limited to, hydrophilic colloidal materials such as, gelatin, albumin, gum arabic, alginate, casein, agar or pectins, or combinations thereof. The projectile can also be made from a synthetic organic compound such as, but not limited to, polystyrene, polypropylene, polyethylene, polycarbonate, polyamide, polysulfane, polyvinylchloride, resinous compounds such as fibreglass or Perspex derivatives, or combinations thereof.

The projectile includes a biologically active agent, a transdermal carrier, and optionally a dye or marker. The biologically active agent can be encapsulated in a controlled-release coating prior to inclusion in the projectile thereby allowing the controlled release of the biologically active agent within an animal to be treated animal, once it has passed transdermally into the blood or lymphatic system of the animal. The controlled-release coating may be selected from controlled release compositions known in the field.

Although it is within the contemplation of the invention that externally administrable biologically active agents may also be included within the projectile, the invention is especially suited to delivering systemic treatments for the treatment of endoparasites or ectoparasites to animals. The treatments may, accordingly, be absorbed by and distributed through the blood or lymphatic system of an animal, once it has been absorbed though the skin of an animal. It is thus an aim of the present invention that the biologically active agents are deliverable to animals by absorption through the skin, and not by a piercing element or needle, so that animals may be treated systemically, substantially without insulting the skin of the animal.

Avermectin and its derivatives are examples of biologically active agents within the contemplation of this invention that constitute a fine, solid powder in their pure form. It is accepted within the art that external administration of such agents in their natural pure form has no material therapeutic effect—prior toxicity studies have established that primate skin types in contact with pure ivermectin absorb less than 1% of the active agent into the bloodstream. The successful development of externally administered 'pour on' and 'spot on' products has demonstrated that therapeutically effective blood uptake levels in animals can only be achieved through external administration of the avermectins in solubilised form. The appropriate solvents known in the art also act as transdermal carriers to enable effective therapeutic amounts of the active pharmaceutical ingredient to be absorbed through the skin and into the bloodstream. The applicants have commissioned specific field and clinical veterinary trials have been carried out to confirm that the administration of non-solubilised ivermectin is equally ineffective to treat animal disease when administered externally by the methods contemplated by the present invention—the results are reported in the Trial Data section below.

The projectile may also include a pharmaceutically acceptable dye or marker composition. The dye or marker is released onto the skin of an animal when the projectile ruptures upon impact with the animal. The dye or marker may be brightly coloured to allow a person administering the treatment to see readily which animals have been treated, and where the projectile has ruptured on the animal. The dye or marker is preferably non-permanent in nature, so that it may no longer be visible on treated animals within a day or two. Preferably, in wildlife management the dye is non-permanent so as not to detract from the aesthetics of game watching.

In one embodiment of the present invention, the dye is a fluorescent dye such that animals, especially nocturnal animals, may be marked or treated at night time. The dyes used in rupturable projectiles currently used in paintball games are generally considered suitable for use in the projectiles of the invention (and are available in a wide variety of colours) provided they do not interfere with the biologically active agent or the transdermal carrier included in the projectile.

It is to be appreciated that the viscosity of the projectile contents should be such that the contents do not run off the skin, fur or coat of the animal prematurely before treatment has occurred. Accordingly, the projectile may also include a thickening agent, such as a starch-like compound, inert polymer, gel, or an oil-based composition such as sesame seed oil, if required.

The biologically active agent or agents contained in the projectile can be in different forms and/or concentrations, depending on the formulation, the carrying capacity, and solubility, and release characteristics desired, for example as neutral molecules, components of molecular complexes, and pharmaceutically acceptable salts, free acids or bases, or quaternary, salts thereof. Simple derivatives of the biologically active agents mentioned herein, such as pharmaceutically acceptable ethers, esters, amides and the like which have desirable retention and release characteristics in vivo, and enzymes, pro-active forms, pro-drugs and the like, can also be employed as required.

The amount of biologically active agent to be complexed with the transdermal carrier will vary depending on the particular active agent, the desired therapeutic effect, and the time span for which the biologically active agent is to be therapeutically effective. Normally, the amount of biologically active agent in the transdermal system can vary from about 0.1% to about 50%, or even from about 0.1% to about 30% by weight based on the dry weight of the total carrier composition. Persons skilled in the field of the invention will be able to determine the adequate amounts required for each application, as required. For examples, for lower dose concentrations, such as with steroidal hormones or corticosteroids, the preferred amount need only be from about 0.1% to about 10%.

It is to be appreciated that the order of steps, the amounts of the ingredients, and the amount and time of mixing may be important process variables which will depend on the specific polymers, marking dyes, biologically active agents, solvents and/or co-solvents, enhancers, additives and/or excipients used in the composition.

The examples provided herein are not to be interpreted as being an exhaustive list of possible integers or embodiments of the invention, and serve merely to illustrate the invention.

The system may include a projectile launcher in the form of an air launcher to be used in combination with the projectile of the invention in treating animals. The projectile launcher can include a magazine or reservoir for accepting a plurality of projectiles. Administering a desired biologically active agent to a target animal is accomplished by a person or user aiming the launcher containing one or more projectiles at the animal, and launching a projectile at the animal with a velocity sufficient to rupture the projectile upon impact with the animal. This allows the contents of the projectile to be splattered onto the skin of the animal, allowing the biologically active agent to be absorbed through the skin of the animal via the transdermal carrier.

The impact of the projectile against the animal also serves to splatter the marker dye, if present, onto the skin of the animal, thereby enabling the user administering the treatment to readily discern whether the animal has been treated, where the site of impact was on the animal (if the site of impact is important to the efficacy and absorption of a specific biologically active agent) and whether the projectile has ruptured successfully or not.

While the projectile of the invention need not be compartmentalized in order to separate the biologically active agent, transdermal carrier, and/or dye composition from one another inside the projectile, it is within the contemplation of the invention that the projectile includes one or more interstitial compartments so as to keep one or more of the components of the projectile from one or more of the other components and only allowing them to mix upon impact with the animal.

The projectiles may have sufficient volume to contain a unit dosage for a certain disease for an animal. The dosage is typically calculated to correspond to a certain minimum weight of animal to which a biologically active agent is to be administered. If larger animals need to be treated, the number of projectiles launched at the animal may be increased accordingly. Alternatively, a single projectile dosage for all animal weights may be preserved by alteration of the formulation concentration of the active pharmaceutical agent.

For example, in order to treat a young impala weighing, say, 50 kg, a single projectile containing a unit dosage may be enough. However, in order to provide a sufficiently efficacious dose to a larger impala estimated to weigh, say, 100 kg, two projectiles may be required.

The launcher can have a selector button which allows one to pre-select the number of projectiles to be launched at the single pull of a trigger of the launcher, thereby allowing larger animals to be treated with the correct dose required, merely by selecting the number of projectiles to be launched simultaneously. This has the advantage that the animal does not have a chance to escape following the first firing of the launcher, as the projectiles reach it substantially simultaneously. Launching one projectile at a time may result in the animal fleeing, making it difficult to track down the same animal and administer a second (or different) dose.

Similarly, it may be necessary to treat an animal with a combination of biologically active agents. This may be accomplished by using a projectile having contained therein a combination of biologically active agents. However, it is not always possible to produce a projectile having two or more different biologically active agents therein, due to adverse reactions occurring between such biologically active agents when they are co-mixed. However, in some instances it may not be feasible to produce a single projectile large enough to accommodate the required unitary doses of two or more biologically active agents. It may also be problematic to launch such a large projectile at the animal with sufficient velocity to rupture the projectile upon impact, but not upon firing.

Alternatively, a user may elect to launch two or more projectiles each containing a different biologically active agent or different set of biologically active agents individually at the animal.

The launcher may be loaded with projectiles in a pre-determined series which may be discharged substantially simultaneously, one may elect to load, say, a projectile containing a systemic anthelmintic, another projectile containing an externally administrable insecticide and a third projectile containing a health supplement (each projectile having different, easily identifiable marker dyes included within the projectile), pre-set the launch to launch three projectiles, and accordingly treat an animal with the three biologically active agents, substantially simultaneously.

It follows thus that a user may elect to load the launcher with several series of such projectiles, following which each time the launcher is aimed at an animal and the trigger is pulled, a selected series of projectiles is discharged.

The invention extends thus to a method of loading a launcher of the invention, by loading a plurality of such series of projectiles, each containing a unit dosage of a biologically active agent, which may be the same, or different.

Results
Projectile
A. Preparation of the Gelatine Base
The ingredients for projectile base were:
water, glycerine and/or sorbitol, and gelatine.
The glycerine and water were weighed in a suitable tank, temperature regulated at about 65° C.
The gelatine was weighed in a separate tank.
The melting apparatus was under vacuum to load the glycerine and water solution, then the vacuum was stopped and the solution was slowly mixed, heating at 80-85° C.
The gelatine was added under vacuum, keeping the blade stirrer at maximum speed.
After 5 minutes of mixing, the vacuum was maintained to remove the air from the projectile base. The vacuum was stopped when there were no air bubbles in the projectile base.
The projectile base was ready to discharge in the gelatine tanks heated at 60° C., applying a pressure with the nitrogen.
B. Preparation of the Fill
The contents of the projectile was either a solution or suspension.
Solution—The pre-weighed medicaments, additives and dissolving liquids are put into a stainless steel "Vessel" and stirred until dissolution was completed. Vacuum was applied. The solution was typically at room temperature but preparations can be heated to form the required solution.
Suspension—The suspending agents were weighted into an heated tank, and stirred during the addition of fats and waxes, that are added from a separate tank where they are kept molten.
To the homogeneous liquid phase are added the powdered ingredients, adding first the more lighter components to avoid a rapid sedimentation.
The mixture was passed through a colloid mill to homogenise the system, and to reduce the particle size of raw materials. Then, the prepared suspension was de-aired by the vacuum, because the presence of air can cause dosage variation at the filling site, since the dosing pump delivers a constant volume. The material was then transferred to a tank.
C. Projectile Manufacture and Filling
The soft gelatine projectile was filled with the composition to form the projectile. This was achieved by feeding two ribbons of gelatine between two die-rolls, into the nip of which the liquid contents of the projectile are fed.
Matching pockets on the rolls allow the fill to distend the gelatine ribbon and mould it to a fixed shape. Simultaneously the edges of the formed projectile are welded together.
The gelatine ribbon is formed in the body of the machine itself. Projectile base from the supply tank flows down by gravity through a cleanline pump and heated tubes to a spreader box. The spreader boxes sit upon a rotating casting drum. The back face of the spreader box (gate) can be raised by a pair of screws so that the width of the slot at the gate of the box, through which the gelatine passes, can be increased or decreased. It is possible to maintain a uniform machine output by changing the film thickness to compensate the changes of the gelatine.
The gelatine structure can be modified:
by temperature
by age
by viscosity
by elasticity (bloom)
The projectile base, when spread onto the casting drums, travels round the periphery over a period of about a minute, cooling and setting as it goes. The drums are cooled by a flow of air coming from the cooling system situated on the back of the machine.

The ribbon is then picked off by a roller and passes between a pair of lubrification rollers, that give the lubrification with a vegetable oil (MIGLYOL) to both sides of the ribbon. Now the two ribbons are ready for the passage through the filling section of the machine.

Two such ribbons are formed at the same time, and pass over the feeder rolls onto the pockets of the die-rolls. As the opposing cavities come towards one another, a unit dose of the contents is injected by one stroke of a double-acting piston pump. The contents reach the cavities through holes drilled in a metal block, the injection segment, which rides under its own weight on the gelatine ribbons entering to the pockets.

The segment surfaces are curved to conform to the roll configuration. As the gelatine ribbon passes the segment, it receives the liquid, deforming into the cavities to accept it.

The edges of the projectile are then sealed, welded evenly by the roll pressure and are cut off all around as the projectile passes between the narrowest part of the inter-roll gap. Below the rolls, the projectiles fall freely into twin belt conveyors, whilst the net continues to travel vertically downwards.

D. Drying Process

The drying of the projectiles is divided in two phases:
in a tumble dryer
in a drying tunnel.

The first phase, which occurs in the tumble dryers, is the relatively rapid removal of the water that is going to be removed.

The rate-limiting factors are mainly:
the boundary layer in the air film surrounding the projectiles, which can be reduced in thickness by increasing the ventilating air rate;
the second is depending of the rate at which water can diffuse through the gelatine of the projectile, and this is a function of:
temperature
amount of plasticiser in the gelatine
nature of the fill.

The projectiles are finish-dried therefore in a drying tunnel, where air is supplied at
a relative humidity of below about 20%, and a temperature of about 22 to 24° C.

Normally the projectiles are held for about 2 to 5 days in such an environment to reduce the moisture content of the gelatine to about 6 to 12%.

For projectile contents containing water-soluble vehicles, the drying time is usually extended because the contents may have adsorbed water from the shell and will release it only slowly.

The rate of drying is typically matched to the slowest diffusion rate-process in the system, otherwise the projectile may fail during drying, or will re-equilibrate on storage.

E. Inspection

After the final drying, ideally every projectile should undergo inspection. The principal defects are selected from critical defects (foreign projectiles, leaking projectiles, under or over weight projectiles) and major & minor defects (misshapes, air bubbles, colour and clarity, greasiness, twins).

A first inspection can be carried out on the drying trays, where the leaking projectiles are easily removed and where possible to check for the other defects.

A second Inspection can be carried out automatically by means of a riddling machine (PHARMASORT 6-12, for example). Automatic inspection, however, will only eliminate projectiles being under or over weight, twins or misshaped.

F. Packaging

Normally projectiles made by the manufacturer are packed in standard bulk packs, the number of projectiles per pack depending upon the size of the projectile. The projectiles can be counted by either electronic or weight counters. The electronic counter, while giving precise count (deviation less than 0.2%), tends to be very slow. The weight counter has a speed of more than 500,000 projectiles/hours. The projectiles are then put into standard 0.125 mm polythene bags and heat-sealed, and then packed in corrugated cardboard cartons, which are placed on pallets.

This package will protect the projectiles for between three and six months from excessive moisture pick up, if stored under normal warehouse conditions.

Formulation and Trials Service

Phase 1
I. Laboratory trials on the received Customer fill material. Check encapsulation suitability.
II. Definition of quali-quantitavive draft master formula (fill and shell).
III. First encapsulation trial, typically with minimum 5 litres of fill preparation.
IV. Preliminary stability test.
V. Points I-IV allow the generation of a preliminary master formula.

Phase 2
Preparation of Final Master Formula.
VI. Master formula must be verified with a pilot trials of maximum 20 litres of fill each.
VII. Final trial to set up the product.
VIII. Stability test.

Suitable Formulations

The tables below illustrate a number of examples of tested and trial formulations, including those with added transdermal enhancers designed to improve systemic take up of active pharmaceutical in a variety of concentrations, examples being propylene glycol (PG) and N-methyl-2 pyrrolidone (NMP).

Formulation 1—Iver 30

| Ingredient | g/l | Descriptor | Approx % v/v |
| --- | --- | --- | --- |
| Ivermectine | 30.0 | Active | 3% |
| N-propyl gallate | | Stabiliser | Minor |
| Thiodipropionic acid | | Stabiliser | Minor |
| Red DC 133 | | Dye | Minor |
| 1-methoxy 2-propanol (glysolv PM/Icinol PM) | | Minor solvent | 10% |
| Ethylene glycol monobytylether (butyl glysolv/butyl icinol) | | Minor solvent | 10-20% |
| Butyl di-glysolv (butyl-icinol) | | Major solvent | 35-50% |

Formulation 2—Iver 15

| Ingredient | g/l | Descriptor | Approx % v/v |
| --- | --- | --- | --- |
| Ivermectine | 15.0 | Active | 3% |
| N-propyl gallate | | Stabiliser | Minor |
| Thiodipropionic acid | | Stabiliser | Minor |
| Red DC 133 | | Dye | Minor |
| 1-methoxy 2-propanol (glysolv PM/Icinol PM) | | Minor solvent | 10% |
| Transcutol | | Minor solvent | 10-20% |
| Butyl di-glysolv (butyl-icinol) | | Major solvent | 35-50% |
| Azone | | | 1-5% |

Formulation 3—Abametin 30

| Ingredient | g/l | Descriptor | Approx % v/v |
| --- | --- | --- | --- |
| Abamectin | 30.0 | Active | 3% |
| N-propyl gallate | | Stabiliser | Minor |
| Thiodipropionic acid | | Stabiliser | Minor |
| Red DC 133 | | Dye | Minor |
| 1-methoxy 2-propanol (glysolv PM/Icinol PM) | | Minor solvent | 10% |
| Transcutol | | Minor solvent | 10-20% |
| PG | | Major solvent | 35-50% |
| Azone | | | 1-5% |

Formulation 4—Abamectin 5

| Ingredient | g/l | Descriptor | Approx % v/v |
| --- | --- | --- | --- |
| Abamectin | 5.0 | Active | 3% |
| N-propyl gallate | | Stabiliser | Minor |
| Thiodipropionic acid | | Stabiliser | Minor |
| Red DC 133 | | Dye | Minor |
| 1-methoxy 2-propanol (glysolv PM/Icinol PM) | | Minor solvent | 10% |
| Transcutol | | Minor solvent | 10-20% |
| NMP | | Major solvent | 35-50% |

Formulation 5—Iver 20

| Ingredient | g/l | Descriptor | Approx % v/v |
| --- | --- | --- | --- |
| Ivermectine | 20.0 | Active | 3% |
| N-propyl gallate | | Stabiliser | Minor |
| Thiodipropionic acid | | Stabiliser | Minor |
| Red DC 133 | | Dye | Minor |
| 1-methoxy 2-propanol (glysolv PM/Icinol PM) | | Minor solvent | 10% |
| Transcutol | | Minor solvent | 10-20% |
| PG | | Major solvent | 35-50% |
| NMP | | | 10% |

Formulation 6—Iver 30 plus

| Ingredient | g/l | Descriptor | Approx % v/v |
| --- | --- | --- | --- |
| Ivermectine | 30.0 | Active | 3% |
| N-propyl gallate | | Stabiliser | Minor |
| Thiodipropionic acid | | Stabiliser | Minor |
| Red DC 133 | | Dye | Minor |
| 1-methoxy 2-propanol (glysolv PM/Icinol PM) | | Minor solvent | 10% |
| Transcutol | | Minor solvent | 10-20% |
| PG | | Major solvent | 35-50% |
| Azone | | | 1-5% |

Animal Trial Protocols

Example 1

Protocol

The present inventors have developed a remote delivery new system (known as the VetCap® Treatment System) for applying treatments such as anthelmintics to wild or unrestrained animals. The system, in a preferred form, comprises a gelatine-based projectile containing a specially formulated anthelmintic, which is fired at animals with a compressed air "launcher" and it ruptures on impact and discharges the anthelmintic onto the skin of the animal.

VetCap® is a registered trade mark of Veterinary Encapsulation Bioscience Pty Ltd used in relation to projectiles and methods of treatment.

The system has been adapted for use in Africa for treating antelope species. Each projectile was designed to treat a 100 kg animal. Drug trials in antelope species and cattle have been carried out in Africa and show that absorption of the active (abamectin) applied in a projectile at the dosage rate of 5 g/l is at least as good as with a traditional Pour On application.

The system is adaptable for use in other animals such deer and cattle.

Formulations for the treatment of animals up to 600 kg in a single dosage projectile can be developed and evaluated, and a series of trials is in progress to determine optimum formulation parameters for this purpose.

Trial Requirements:

Compare the transdermal uptake of a formulation of the Iver 30 (Ivermectin 30 g/l i.e. one projectile treats a 600 kg animal) and Iver15 (Ivermectin 15 g/l i.e. one projectile treats a 300 kg animal) applied using a pour on method, with the same dosages applied with a projectile containing the same endectocide. Blood sampling at intervals after treatment and a pharmacokinetic study show the plasma levels of the endectocide are substantially the same (i.e. bio-equivalence) in treated cattle.

Number of Animals Per Group:

Protocols for studies on anthelmintics in domestic animals usually specify a minimum of six animals per treatment group. However, in a pharmacokinetic study, if there are wide variations in plasma levels of the bioactive substance, this may not show statistically significant "bioequivalence". Trials with pour-on formulations in cattle often show great variability, but this appears to be largely because cattle treated with pour on often lick themselves and each other, leading to plasma levels resulting from oral as well as transcutaneous absorption.

Because this is only a "proof of concept" trial, n=3 was sufficient to show substantially similar absorption from the projectile according to the present invention compared with pour on treatment i.e. total number of cattle was 12.

Group A (3 cattle): 10 ml Ivermectin formulation poured on to the surface of the skin (30 g/l) to treat up to 600 kg animal.

Group B (3 cattle): One 10 ml projectile containing Ivermectin (30 g/l) to treat up to 600 kg applied using the system according to the present invention.

Group C (3 cattle): 10 ml Ivermectin formulation poured on to the surface of the skin (15 g/l) to treat up to 300 kg Group D (3 cattle): One 10 ml projectile containing the Ivermectin (15 g/l) to treat up to 300 kg applied using the treatment system according to the present invention.

Pour-on doses to be drawn from existing VetCap® Iver 30 and Iver 15 projectiles using a syringe, the needle is then to be removed and contents ejected directly onto each animal in a single location (preferably in an approximately 20 centimetre circular patch on the upper flank of the animal in a similar area to where the animal will be shot with the projectile).

VetCap® projectiles to be fired from 15 metres at the flank of each animal to be treated. If the projectile misses the animal, the treatment is to be repeated. If there is a partial "hit", then the animal will be discarded from the group and replaced by another equivalent animal that is then treated fully.

Pharmacokinetic Study

Prior to analysis of the blood samples, one Iver30 projectile and one Iver15 projectile from the same batch as that used to for the field trial was tested by the laboratory to ensure that the Ivermectin levels present in the formulation were stable at 30 g/l and 15 g/l respectively. Once confirmed the laboratory tested the blood samples.

Blood sampling (2×10 ml "green top" heparinised blood sample):

Sample all groups (A, B, C, D) on days 0, 1, 2, 3, 4.

Blood samples were spun down as soon as possible, serum extracted and after collection and the duplicate plasma samples frozen at −20 C. At the completion of the trial, one set of samples was sent to the analytical testing laboratory for assaying for Ivermectin. The duplicate set was retained until the first set had been analysed and results assessed, in case the samples are lost in transit or there is any need to repeat the analyses.

Pretrial:

Ensure all animals are healthy.

Ensure that no anthelmintic is given in 8 weeks prior to trial starting.

Ensure all animals have individual eartags

Ensure yarding systems are adequate and there is adequate provision for feed throughout the 6 week trial Trial Schedule:

Day-7 Check equipment, test ballistics, target practice, measure impact etc

Day-7 Check Cattle, health, tags, weigh, allocate to groups

Day 0 Blood sample Groups (A, B, C, D) weigh, treat groups

Day 1 Blood sample Groups (A, B, C, D)

Day 2 Blood sample Groups (A, B, C, D)

Day 3 Blood sample Groups (A, B, C, D)

Day 4 Blood sample Groups (A, B, C, D)

Day 7 Blood sample, Groups (A, B, C, D)

Day 14 Blood sample, Groups (A, B, C, D)

Day 28 Blood sample, Groups (A, B, C, D)

Day 35 Blood sample, Groups (A, B, C, D)

Day 42 Blood sample, Groups (A, B, C, D)

Trial ends and animals remained at the research facility for a minimum of 5 weeks before resale or slaughter (WHP 35 days).

Results confirmed preliminary work that the system according to the present invention provided desired levels of treatment.

Trial Data

The following independent trials were conducted at the South African Agricultural Research Council establishment at Irene, Pretoria under the direction of the SA Registrar of Veterinary Medicines and in accordance with product registration procedures:

The purpose of the trial was to establish the efficacy of biologically active agent when administered by the system according to the present invention in treating cattle for the endo-parasite wireworm.

Two cattle of similar age and weight (~200 kg) were infected with wireworm parasite to the level of 6000 to 8000 worm eggs per gram of faeces. One cow was treated with the biologically active agent in its 'pour on' form and the other cattle were treated with two dosage projectiles fired from a distance of approx 20 metres with a $CO_2$ propelled launcher with an impact velocity of about 130 ft/sec.

Each projectile was spherical and made from soft gelatine compound with the shell being of about 2 mm thick. The size was sufficient to hold about 10 ml of the liquid biologically active agent comprising the following constituent:

10 mg of abamectin (at a dosage concentration of 1 mg per 10 kg of body mass)

5% solution of the solvent/transdermal carrier propylene glycol (the proprietary brand Icinol)

a standard turquoise, inert pharmaceutical colorant known as FC & D blue

The impact area of the ruptured projectiles was the hind quarter and lower neck/shoulder of the cattle.

The cattle were slaughtered 3 weeks after treatment and the stomach contents/linings examined under laboratory conditions. The cow treated by projectile administration was found to be 100% free of internal parasite infection—the other treated cow was approx 96% free of parasite.

This test showed that the treatment method according to the present invention met with industry efficacy standards for treatment of endo-parasites when used in conjunction with the transdermal formulation.

The enhanced efficacy of the projectile method of administration in this test may be attributable directly to the delivery method. This involved subcutaneous bruising around the impact site. This caused dilation of the blood vessels and it is postulated that this reaction enhances the treatment efficacy through better absorption of the pharmaceutical ingredients into the blood stream.

Further independent trials were carried out in South Africa substantially in accordance with the above stated protocol on 6 cattle. The research objective of this trial was to determine the extent (if any) to which administration of pure (non-solubilised) ivermectin by the methods contemplated by the present invention were effective to treat parasite disease in cattle.

The subject cattle were treated with external delivery of non-solubilised ivermectin in soya oil suspension fluid (containing no known solvent or other transdermal carrier agent) within a standard gelatin projectile as described. The ivermectin content was the equivalent of the standard 5 gram per litre 'pour on' solutions.

Blood test analysis revealed no significant systemic take up of the ivermectin, and effective therapeutic blood level was not achieved. This trial confirmed the accepted scientific opinion of those practised in the art—namely, that the external administration of non-solubilised ivermectin is ineffective for therapeutic treatment purposes.

Example 2

Look and See Trial of VetCap® Projectile on 2 *Bos Taurus* Weaner Calves

The purpose of the trial was to determine the efficacy against ticks of a formulation containing 0.5% solubilised abamectin and transdermal solvent encapsulated inside a gelatine projectile (with each bolus containing 10 ml of the composition) applied externally onto the calves by means of a specially designed compressed airgun, similar to a dart gun or paintball marker termed a VetCap® 'launcher'. Efficacy of the test article against ticks on calves was assessed for registration purposes in South Africa. The test active was applied at a dose rate of a 10 ml bolus/100 kg body weight and animals were observed and ticks counts done before treatment and again after 7 days.

The test active was applied at a rate of one 10 ml VetCap® projectile (VetCap®) for animals weighing up to 100 kg and two 10 ml VetCaps for animals weighing between 100 to 200 kg. The projectiles containing the test active were loaded into the VetCap® launcher and shot at the animal to be treated from a distance of about 2 m.

Tick counts were done on day 0, before treatment; and on day 7 after treatment according to the applicable standard operating procedure. Ticks were counted and identified in situ. In each case ticks on the whole animal were counted. No adverse reactions to the test active occurred. The percentage efficacy of VetCap® applied as a ballistic bolus, against adult *Boophilus*, was 92.7%. Percentage efficacy against immature *Boophilus* was 98.6%.

Example 3

VetCap® Tolerance in Sheep and Goats

The purpose of this trial was to determine the safety of an abamectin formulation applied using the VetCap® treatment system (Ballistic Boli) in sheep and goats. The formulation containing 0.5% solubilised abamectin and transdermal solvent was encapsulated inside a gelatine projectile with each bolus containing 10 ml of the compound. The formulation may cause adverse symptoms in animals and safety had to be assessed for registration purposes in South Africa. Ten healthy sheep and 10 healthy goats were treated with the test article. As all the animals were treated, no provision for ranking, allocation to experimental groups and statistical procedures was required. The test article was applied at a rate of one 10 ml bolus for animals weighing up to 100 kg and two 10 ml boli for animals weighing between 100 to 200 kg. The VetCap® boli containing the test active were loaded into a specially designed compressed air rifle (VetCap® 'launcher') and shot at the animal to be treated from a distance of about 2 m as set out in the table below:

Criteria to be assessed are shown in the table below. The scoring was as follows:
0=Normal; 1=Mild; 2=Moderate; 3=Severe; 4=Extremely severe No adverse symptoms or reactions to the test active were observed in any of the animals during the trial. The test active would therefore be regarded as safe for use in the trial animals, when administered using the VetCap® treatment system administration method in ballistic bolus form.

Example 4

Histological Impact Study of VetCap® in Ovine, Caprine and Bovine

The objective of this study was to determine the histological impact of an abamectin formulation in ovine, caprine and bovine. The formulation containing 0.5% solubilised abamectin and transdermal solvent was encapsulated inside a gelatine projectile with each bolus containing 10 ml of the compound. The bolus can be shot onto the body of an animal by using a specially designed compressed air rifle, similar in operation to a dart gun or paintball marker (VetCap® launcher).

Histological evaluation of skin, subcutis and muscle specimens, from sites of bolus impact, was done. Twelve animals were involved in the trial, four of each species. The boli were applied to two animals of each species from a distance of 1 m at a dose rate of 1 bolus per animal and to the other two animals of each species from a distance of 5 m at the same dose rate, The breeds involved in the study were Dorper Hair Sheep, indigenous goats and Nguni cattle calves.

The experimental lay-out and sampling schedule is shown in the following tables.

The sheep were shorn before application of the boli, but not the goats and calves, as their hair was unlikely to lessen the impact of the boli. Twenty-four hours after treatment, two animals from each species, one shot from a distance of 1 m and the other shot from a distance of 5 m, were necropsied and biopsies taken. One sample was taken from each animal and placed in formalin. The same schedule was followed 48 hours after treatment. Samples were taken to pathologist after completion of the animal phase.

TABLE 1

Histological evaluation of ovine samples:

| Animal number | Sample number | Shooting distance | Time interval after treatment | Sample type | Histological evaluation |
|---|---|---|---|---|---|
| 2C | A | 5 m | 24 h | Skin | Histologically normal |
|  |  |  |  | Subcutaneous tissue | Histologically normal |
|  |  |  |  | Skeletal muscle | One small focal area revealed a mild infiltration of lymphocytes in the interstitium of the muscle tissue |
| C | B | 1 m | 24 h | Skin | Histologically normal |
|  |  |  |  | Subcutaneous tissue | Histologically normal |
|  |  |  |  | Skeletal muscle | Two small focal areas of mainly lymphocytic infiltration of a very mild nature in the interstitial tissue between the muscle fibres |
| 2D | C | 5 m | 48 h | Skin | Histologically normal |
|  |  |  |  | Subcutaneous tissue | Not present |
|  |  |  |  | Skeletal muscle | Histologically normal |
| D | D | 1 m | 48 h | Skin | Mild peri vascular infiltration of lymphocytes and plasma cells in the superficial dermis |

TABLE 1-continued

Histological evaluation of ovine samples:

| Animal number | Sample number | Shooting distance | Time interval after treatment | Sample type | Histological evaluation |
|---|---|---|---|---|---|
| | | | | Subcutaneous tissue | Multifocal nodular areas revealed dense fibroblastic proliferation with larger numbers of lymphocytes, plasma cells and macrophages associated with the reaction. Moderate numbers of lymphocytes and plasma cells were present perivascularly in these areas. Two of the areas contained foreign material compatible with plant/hair-type material |
| | | | | Skeletal muscle | Histologically normal |

TABLE 2

Histological evaluation of caprine samples:

| Animal number | Sample number | Shooting distance | Time interval after treatment | Sample type | Histological evaluation |
|---|---|---|---|---|---|
| 2A | F | 5 m | 24 h | Skin | A focal area of the skin section revealed a moderate perivascular lymphoplasmacytic infiltration in the superficial dermis. There is moderately increased amounts of collagen in the superficial dermis. |
| | | | | Subcutaneous tissue | Histologically normal |
| | | | | Skeletal muscle | Histologically normal |
| A | E | 1 m | 24 h | Skin | Mildly increased amounts of fibroblasts and collagen in the superficial dermis |
| | | | | Subcutaneous tissue | Histologically normal |
| | | | | Skeletal muscle | Histologically normal |
| 2B | H | 5 m | 48 h | Skin | Moderate perivascular lymphoplasmacytic infiltrations were evident in superficial blood vessels of the dermis. Moderate to severe orthokeratotic hyperketosis was also evidence in the skin section as well as moderate increase in superficial dermal collagen |
| | | | | Subcutaneous tissue | Histologically normal |
| | | | | Skeletal muscle | Histologically normal |
| B | G | 1 m | 48 h | Skin | A moderate lymphoplasmacytic perivascular infiltration was visible in the superficial dermis of the skin section. Severe orthokeratotic hyperkeratosis was also evident and moderate increase in superficial dermal collagen |
| | | | | Subcutaneous tissue | Histologically normal |
| | | | | Skeletal muscle | Histologically normal |

TABLE 3

Histological evaluation of bovine samples:

| Animal number | Sample number | Shooting distance | Time interval after treatment | Sample type | Histological evaluation |
|---|---|---|---|---|---|
| 2E | J | 5 m | 24 h | Skin | Mild perivascular lymphoplasmacytic infiltrates were visible in the superficial dermis |
|  |  |  |  | Subcutaneous tissue | Histologically normal |
|  |  |  |  | Skeletal muscle | Histologically normal |
| E | I | 1 m | 24 h | Skin | A moderate perivascular infiltration of mast cells and eosinophills were visible in around the superficial blood vessels of the dermis |
|  |  |  |  | Subcutaneous tissue | Histologically normal |
|  |  |  |  | Skeletal muscle | Histologically normal |
| 2F | L | 5 m | 48 h | Skin | Mild perivascular infiltrations of lymphoplasmacytic, plasma cells as well as a small number of neutrophils were evident in the dermis |
|  |  |  |  | Subcutaneous tissue | Histologically normal |
|  |  |  |  | Skeletal muscle | Histologically normal |
| F | K | 1 m | 48 h | Skin | Moderate numbers of lymphocytes, plasma cells as well as eosinophils and few mast cells were evident perivascularly surrounding the superficial blood vessels of the dermis |
|  |  |  |  | Subcutaneous tissue | Histologically normal |
|  |  |  |  | Skeletal muscle | One small focal area revealed a mainly lymphocytic infiltration in the interstitial tissue |

The above results indicate no serious injury or unacceptable levels of tissue damage caused to any of the test subjects. The method of delivery using the VetCap® treatment system according to the present invention was therefore deemed safe under the test conditions.

Example 5

The Remote Treatment of Ticks on Nguni-Cross Calves (*Bos taurus* & *Bos indicus* Traits) with VetCap®

The purpose of the trial was to determine the efficacy against ticks of a 0.5% (m/v) abamectin formulation applied topically in calves by means of a specially designed compressed airgun (VetCap® launcher). A formulation containing solubilised abamectin and transdermal carriers was encapsulated in a bolus with a gelatine projectile, containing 10 ml abamectin, which was shot onto the body of the test animals by means of a the VetCap® launcher. Efficacy of the test active against ticks on calves was assessed for registration purposes in South Africa. The test active was applied at a dose rate of a 10 ml bolus/100 kg body weight and animals were observed and ticks counts done before treatment and again after 7 days.

Administration of the test active took place according to the table. The test active was applied at a rate of one 10 ml bolus for animals weighing up to 100 kg and two 10 ml boll for animals weighing between 100 to 200 kg. The boli containing the test active were loaded into the VetCap® launcher and shot at the animal to be treated from a distance of about 12 m.

Example 6

Degradation of VetCap® Containing Abamectin in the Environment

An antiparasitic formulation containing solubilised abamectin and transdermal carriers was encapsulated in a bolus with a gelatine projectile, containing 10 ml abamectin. The detailed descriptions are shown in Table 4. Discolouration took place, especially in the sun (faster and more pronounced). The broken boli shrivelled and deteriorated fast, especially the one in the sun. Both the whole and unbroken boli in the sun showed faster discolouration and deterioration when compared to the ones placed in the shade. Leakage of content was observed after 21 days in the whole bolus placed in the sun and at 28 days in the whole bolus placed in the shade. The process was photographed and recorded. Degradation of the VetCap® projectile led to only pieces of shell being present after 28 days in all the cases, whether left in the sun or shade and therefore this is determined as its maximum exposure limit.

TABLE 4

Degradation of projectile
Observations of the whole VetCap ® bolus

| Placement | Day 0 | Day 7 | Day 14 | Day 21 | Day 28 |
|---|---|---|---|---|---|
| Shade | Blue Unbroken Diameter ±3 cm | Blue Unbroken Dented No leakage Diameter ±3 cm | Blue Unbroken Larger dent No leakage Diameter ±3 cm | Blue Unbroken Larger dent No leakage Diameter ±3 cm | Blue Leakage occurred Larger dent Diameter ±2 cm |
| Sun | Blue Unbroken Diameter ±3 cm | White discolouration Diameter ±3 cm | White discolouration Large dents No leakage | White discolouration Leakage Diameter ±2.6 cm | White discolouration Shrivelled Diameter ±2 cm |
| Shade | Light blue discolouration Empty | Light blue discolouration Shell broken and shrivelled | Whitish discolouration Shell broken into smaller pieces | Whitish discolouration Shell broken into smaller pieces | Small pieces of shell Transparent white |
| Sun | Light blue discolouration Empty | Broken pieces of shell Transparent white | Broken pieces of shell Transparent white | Broken pieces of shell Transparent white | Brownish pieces of shell |

Example 7

The Efficacy of VetCap® Against the Nematode Parasites of Blesbuck

The game farming industry is in need of registered anthelmintics for game animals, but for the registration of an anthelmintic it is required by the registering authorities that the efficacy of such an anthelmintic be validated in the target animal species before it can be registered. A previous efficacy study was done with a medicated food additive in impala, but great difficulty was experienced in getting the wild animal to take medicated feed, therefore it was decided to attempt an alternative method of applying abamectin in order to combat parasitic challenge.

A specially prepared antiparasitic formulation containing solubilised abamectin and transdermal carriers was encapsulated in a bolus with a gelatine projectile, containing 10 ml abamectin, which was shot onto the body of the test animals by means of a specially designed compressed air rifle (Vet-Cap® launcher). The objective of the study was to determine the anthelmintic efficacy of the abamectin formulation delivered using the treatment system according to the present invention against the nematode parasites of blesbuck.

The abamectin formulations in the projectiles were applied to 6 blesbuck at a rate of 1 bolus/10 ml per kg, while a further 6 blesbuck were kept untreated as control. The blesbuck were slaughtered and the nematode parasites in the abomasums recovered, counted and compared to calculate the effect of the abamectin formulation applied using the test system. On day 7 after treatment, the animals in groups 1 and 2 were slaughtered and the abomasums collected and processed to recover nematode parasites. Only abomasal parasites were recovered in the treated animals and the bolus formulation was 98.37% effective against the *Haemonchus* spp. present. The high efficacy rating is an indication of the potential of this form of treatment for game animals is illustrated Table 5 below.

TABLE 5

Efficacy of projectile

| Experimental Group | Animal Number | *Haemonchus* spp. recovered | | |
|---|---|---|---|---|
| | | Immature | Adult | Total |
| Group 2 Untreated Control | 2 | 20 | 205 | 225 |
| | 4 | 45 | 170 | 215 |
| | 6 | 15 | 205 | 220 |
| | 8 | 0 | 40 | 40 |
| | 10 | 115 | 240 | 355 |
| | 12 | 50 | 125 | 175 |
| | Geometric Mean | | | 172.79 |
| group 1 Virbamax Ballistic Ball | 1 | 0 | 5 | 5 |
| | 3 | 0 | 20 | 20 |
| | 5 | 0 | 0 | 0 |
| | 7 | 0 | 0 | 0 |
| | 9 | 5 | 0 | 5 |
| | 11 | 0 | 0 | 0 |
| | Geometric Mean | | | 2.82 |
| | Anthelmintic Efficacy % | | | 98.37 |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A remote treatment delivery system for an animal comprising:
    a dosage projectile adapted to deliver a biologically active agent to the animal substantially without piercing the skin of the animal and containing a biologically active agent and a transdermal carrier in liquid or gel form, wherein the agent and the carrier are encapsulated in one or more encapsulating agents; and
    wherein the encapsulating agents forms a frangible shell.

2. The delivery system according to claim 1 wherein the biologically active agent is an anthelmintic, acaricide or an anti-parasitic composition or compound.

3. The delivery system according to claim 2 wherein the biologically active agent is a macrocyclic lactone selected from the group consisting of ivermectin, abamectin, eprinomectin, moxidectin, selamectin, doramectin, and emamectin benzoate.

4. The delivery system according to claim 2 wherein the biologically active agent is a synthetic pyrethroid selected from the group consisting of flumethrin, deltamethrin, cypermethrin, cyfluthrin, fenvalerate, alphacypermethrin and pyrethrin.

5. The delivery system according to claim 2 wherein the biologically active agent is an insect growth regulator selected from the group consisting of yriproxifen, methoprene, cyromazine, lufenuron, diflubenzuron, fluazuron, and dicyclanil.

6. The delivery system according to claim 1, wherein the biologically active agent is an amidine.

7. The delivery system according to claim 2, wherein the acaricide is an organophosphorous acaricide.

8. The delivery system according to claim 2, wherein the biologically active agent is selected from the group consisting of fipronil, imidacloprid, rotenone, Mg flurosilicate, piperonyl butoxide, spinosyns, benzimidazoles and amino-acetonitrile derivatives.

9. The delivery system according to claim 1, wherein the biologically active agent is a hormone.

10. The delivery system according to claim 1, wherein the biologically active agent is an anti-infective, anaesthetic, analgesic, anti-inflammatory, antibiotic, anti-fungal, antihistamine, antiviral, antioxyltic, β-adrenergic agonist, bronchodilator, cardioactive, CNS stimulating, cholinergic, antcholinergic, anti-emetic, muscle-relaxing or antimicrobial agent.

11. The delivery system according to claim 1, wherein the biologically active agent is a health supplement.

12. The delivery system according to claim 11, wherein the health supplement is a vitamin or mineral.

13. The delivery system according to claim 1, wherein the biologically active agent is a vaccine or immunogenic compound.

14. The delivery system according to claim 1, further comprising one or more adjuvants.

15. The delivery system according to claim 1, wherein the transdermal carrier is selected from the group consisting of isopropyl alcohol; dipropylene glycol methyl-ether; butylated hydroxytoluene dipropylene glycol monomethyl-ether; methylene chloride; diethyl ether, ethanol, acetonitrile, ethyl acetate, benzyl alcohol and a combination of natural oils, ethylene glycol, propylene glycol, dimethyl polysiloxane (DMPX), oleic acid, caprylic acid, 1-octanol, ethanol (denatured or anhydrous), liposomal compositions, plant oils, acrylic polymers, rubber-based polymers, polysiloxane-based polymers, polyvinylpyrrolidone-based polymers, dimethylsulfoxide (DMSO), dimethylformamide (DMF), lecithin, bi-component vesicular aggregates, ethosomes, azone, castor oil derivatives, jojoba oil derivatives, corn oil derivatives, and emu oil derivatives.

16. The delivery system according to claim 15, wherein the transdermal carrier is propylene glycol, DMSO, alcohol, or a penetrant adjuvant.

17. The delivery system according to claim 1, further comprising a marker able to mark the skin, coat or fur of an animal.

18. The delivery system according to claim 17, wherein the marker is capable of marking the animal for a period of about 1 hour to about 72 hours.

19. The delivery system according to claim 18, wherein the marker marks the animal for a period of about 24 to 48 hours.

20. The delivery system according to claim 17, wherein the marker is a cosmetic colorant, pigment, or dye.

21. The delivery system according to claim 20, wherein the marker is a liquid dye, powder dye, water soluble dye, infrared dye, ultraviolet dye, or a dye that glows in the dark.

22. The delivery system according to claim 1, wherein the frangible shell is made of gelatine, linear polymers, or polystyrene derivatives, thin-walled plastics materials, hydrophilic colloidal materials including gelatin, albumin, gum arabic, alginate, casein, agar or pectins, synthetic organic compounds, resinous compounds, or combinations thereof.

23. The delivery system according to claim 15 wherein the plant oil is selected from the group consisting of *Aloe vera* oil, sesame seed oil, and derivatives thereof.

24. The delivery system according to claim 15 wherein the castor oil derivative is ethoxylated castor oil.

25. The delivery system according to claim 1, wherein the animal is a wildlife or game animal, a livestock animal, or a feral animal.

26. The delivery system according to claim 25, wherein the wildlife or game animal is selected from deer and buffalo.

27. The delivery system according to claim 25, wherein the livestock animal is selected from the group consisting of cattle, pigs, goats, sheep, and horses.

28. The delivery system according to claim 25, wherein the feral animal is selected from the group consisting of dogs, goats, and pigs.

* * * * *